United States Patent
Golemon, Jr. et al.

(10) Patent No.: US 12,370,062 B2
(45) Date of Patent: Jul. 29, 2025

(54) INDEPENDENTLY IMPLANTABLE SENSORS FOR ORTHOPEDIC IMPLANTS

(71) Applicant: Zimmer, Inc., Warsaw, IN (US)

(72) Inventors: Nathan Golemon, Jr., Warsaw, IN (US); John Kyle Mueller, Warsaw, IN (US); Jeffrey E. Bischoff, Warsaw, IN (US); Matthew Vanderpool, Warsaw, IN (US); Louis-Philippe Amiot, Montreal (CA); Annelise Galloway, Winona Lake, IN (US); Pierre Couture, Montreal (CA); Ted Spooner, Grand Rapids, MI (US)

(73) Assignee: Zimmer, Inc., Warsaw, IN (US)

( * ) Notice: Subject to any disclaimer, the term of this patent is extended or adjusted under 35 U.S.C. 154(b) by 571 days.

(21) Appl. No.: 17/832,271

(22) Filed: Jun. 3, 2022

(65) Prior Publication Data

US 2022/0387186 A1    Dec. 8, 2022

Related U.S. Application Data

(60) Provisional application No. 63/197,094, filed on Jun. 4, 2021.

(51) Int. Cl.
*A61F 2/46* (2006.01)
*A61B 5/00* (2006.01)
(Continued)

(52) U.S. Cl.
CPC ............ *A61F 2/461* (2013.01); *A61B 5/4504* (2013.01); *A61B 5/686* (2013.01); *A61B 5/6878* (2013.01);
(Continued)

(58) Field of Classification Search
CPC ...... A61F 2/461; A61F 2/3854; A61F 2/3859; A61F 2/389; A61F 2/4666;
(Continued)

(56) References Cited

U.S. PATENT DOCUMENTS 6,245,109 B1    6/2001    Mendes et al.
6,573,706 B2    6/2003    Mendes et al.
(Continued)

FOREIGN PATENT DOCUMENTS

EP    4346562    4/2024
WO    2022256696    12/2022

OTHER PUBLICATIONS

"International Application Serial No. PCT US2022 032228, Invitation to Pay Additional Fees mailed Nov. 15, 2022", 16 pgs.
(Continued)

*Primary Examiner* — Ankit D Tejani
*Assistant Examiner* — Joshua Brendon Solomon
(74) *Attorney, Agent, or Firm* — SCHWEGMAN LUNDBERG & WOESSNER, P.A.

(57) ABSTRACT

A surgical sensor system for collecting internal patient data comprises a sensor module comprising a housing and a sensor disposed within the housing, and an attachment device comprising a socket for receiving the housing and an exterior anchor feature for attaching the attachment device to biological matter. A method of implanting a sensor module for use with an orthopedic implant device comprises making an insertion portal in anatomy of a patient, positioning a sensor module in the anatomy in a first position relative to the insertion portal, and positioning an orthopedic implant in the anatomy in a second position relative to the insertion portal such that the orthopedic implant is separate from the sensor module.

20 Claims, 6 Drawing Sheets

(51) Int. Cl.
*A61F 2/38* (2006.01)
*A61B 5/01* (2006.01)
*A61B 5/145* (2006.01)
*A61B 17/00* (2006.01)
*A61B 17/88* (2006.01)

(52) U.S. Cl.
CPC .......... *A61F 2/3854* (2013.01); *A61F 2/3859* (2013.01); *A61F 2/389* (2013.01); *A61B 5/01* (2013.01); *A61B 5/14539* (2013.01); *A61B 2017/00084* (2013.01); *A61B 2017/00734* (2013.01); *A61B 2017/883* (2013.01); *A61B 2560/0406* (2013.01); *A61B 2562/222* (2013.01); *A61F 2002/4666* (2013.01)

(58) Field of Classification Search
CPC .............. A61F 2/30942; A61F 2/30217; A61F 2/30331; A61F 2/30879; A61F 2/4657; A61F 2/4684; A61F 2/30667; A61F 2/3067; A61F 2/30884; A61F 2002/4666; A61F 2002/30217; A61F 2002/30331; A61F 2002/30879; A61F 2002/30667; A61F 2002/3067; A61F 2002/30884; A61B 5/4504; A61B 5/686; A61B 5/6878; A61B 5/01; A61B 5/14539; A61B 5/0538; A61B 5/1126; A61B 5/14507; A61B 2017/00084; A61B 2017/00734; A61B 2017/883; A61B 2560/0406; A61B 2562/222

See application file for complete search history.

(56) References Cited

U.S. PATENT DOCUMENTS

| | | | |
|---|---|---|---|
| 6,706,005 B2 | 3/2004 | Roy et al. | |
| 6,821,299 B2 | 11/2004 | Kirking et al. | |
| 6,918,308 B2 | 7/2005 | Biedermann et al. | |
| 7,097,662 B2 | 8/2006 | Evans, III et al. | |
| 7,210,240 B2 | 5/2007 | Townsend et al. | |
| 7,256,695 B2 | 8/2007 | Hamel et al. | |
| 7,395,167 B2 | 7/2008 | Frolik | |
| 7,412,897 B2 | 8/2008 | Crottet et al. | |
| 7,470,288 B2 | 12/2008 | Dietz et al. | |
| 7,478,108 B2 | 1/2009 | Townsend et al. | |
| 7,575,602 B2 | 8/2009 | Amirouche et al. | |
| 7,578,821 B2 | 8/2009 | Fisher et al. | |
| 7,587,945 B2 | 9/2009 | Crottet et al. | |
| 7,672,781 B2 | 3/2010 | Churchill et al. | |
| 7,786,867 B2 | 8/2010 | Hamel et al. | |
| 7,831,403 B2 | 11/2010 | Frolik | |
| 7,842,092 B2 | 11/2010 | Otto et al. | |
| 7,918,887 B2 | 4/2011 | Roche | |
| 7,970,734 B2 | 6/2011 | Townsend et al. | |
| 8,029,566 B2 | 10/2011 | Lozier et al. | |
| 8,032,486 B2 | 10/2011 | Townsend et al. | |
| 8,065,927 B2 | 11/2011 | Crottet et al. | |
| 8,197,549 B2 | 6/2012 | Amirouche et al. | |
| 8,956,418 B2 | 2/2015 | Wasielewski et al. | |
| 10,492,686 B2 | 12/2019 | Hunter et al. | |
| 10,531,826 B2 | 1/2020 | Wasielewski et al. | |
| 2003/0069644 A1* | 4/2003 | Kovacevic | A61F 2/389 623/18.11 |
| 2007/0004994 A1* | 1/2007 | Sherman | A61F 2/30 623/18.12 |
| 2007/0233267 A1 | 10/2007 | Amirouche et al. | |
| 2007/0234819 A1 | 10/2007 | Amirouche et al. | |
| 2007/0239165 A1 | 10/2007 | Amirouche | |
| 2008/0065225 A1 | 3/2008 | Wasielewski et al. | |
| 2009/0005708 A1 | 1/2009 | Johanson et al. | |
| 2009/0138019 A1 | 5/2009 | Wasielewski | |
| 2009/0149963 A1* | 6/2009 | Sekel | A61F 2/30721 623/20.15 |
| 2009/0287310 A1 | 11/2009 | Fisher et al. | |
| 2009/0299483 A1 | 12/2009 | Amirouche et al. | |
| 2010/0198275 A1 | 8/2010 | Chana et al. | |
| 2010/0217156 A1 | 8/2010 | Fisher et al. | |
| 2010/0249533 A1 | 9/2010 | Pierce et al. | |
| 2010/0249534 A1 | 9/2010 | Pierce et al. | |
| 2010/0249535 A1 | 9/2010 | Pierce et al. | |
| 2010/0249658 A1 | 9/2010 | Sherman | |
| 2010/0249659 A1 | 9/2010 | Sherman et al. | |
| 2010/0249660 A1 | 9/2010 | Sherman et al. | |
| 2010/0249777 A1 | 9/2010 | Sherman et al. | |
| 2010/0249789 A1 | 9/2010 | Rock et al. | |
| 2010/0249790 A1 | 9/2010 | Roche | |
| 2010/0250276 A1 | 9/2010 | Pierce et al. | |
| 2010/0326210 A1 | 12/2010 | Stein et al. | |
| 2010/0326211 A1 | 12/2010 | Stein | |
| 2010/0328077 A1 | 12/2010 | Stein | |
| 2010/0328098 A1 | 12/2010 | Stein et al. | |
| 2010/0331633 A1 | 12/2010 | Stein | |
| 2010/0331682 A1 | 12/2010 | Stein et al. | |
| 2010/0331683 A1 | 12/2010 | Stein et al. | |
| 2010/0331718 A1 | 12/2010 | Stein | |
| 2010/0331733 A1 | 12/2010 | Stein | |
| 2010/0331734 A1 | 12/2010 | Stein | |
| 2010/0331736 A1 | 12/2010 | Stein | |
| 2010/0331737 A1 | 12/2010 | Stein et al. | |
| 2010/0331894 A1 | 12/2010 | Stein | |
| 2010/0332152 A1 | 12/2010 | Stein | |
| 2011/0118566 A1 | 5/2011 | Roche | |
| 2011/0124981 A1 | 5/2011 | Roche | |
| 2011/0160616 A1 | 6/2011 | Stein et al. | |
| 2011/0160738 A1 | 6/2011 | Mcintosh et al. | |
| 2012/0216611 A1 | 8/2012 | Stein et al. | |
| 2014/0222156 A1* | 8/2014 | Nevins | A61F 2/3886 623/20.34 |
| 2016/0166201 A1* | 6/2016 | Stein | A61B 5/686 600/302 |
| 2016/0192878 A1* | 7/2016 | Hunter | A61B 5/0031 623/20.14 |
| 2018/0184944 A1 | 7/2018 | Bodewes et al. | |
| 2019/0350522 A1 | 11/2019 | Bailey et al. | |
| 2021/0267764 A1* | 9/2021 | Stocks | A61F 2/389 |

OTHER PUBLICATIONS

"International Application Serial No. PCT US2022 032228, PCT Search Report, mailed Jan. 13, 2023", 8 pgs.
"International Application Serial No. PCT US2022 032228, Written Opinion mailed Jan. 13, 2023", 14 pgs.
"International Application Serial No. PCT US2022 032228, International Preliminary Report on Patentability mailed Dec. 14, 2023", 14 pgs.
"Australian Application Serial No. 2022285762, First Examination Report mailed Jul. 15, 2024", 4 pgs.
"Australian Application Serial No. 2022285762, Response filed Aug. 30, 2024 to First Examination Report mailed Jul. 15, 2024", 22 pgs.
"European Application Serial No. 22747157.0, Response Filed Jul. 1, 2024 to Communication pursuant to Rules 161(1) and 162 EPC mailed Jan. 11, 2024", 14 pgs.
"European Application Serial No. 16163921.6, Communication under Rule 164(2)(a) EPC mailed Sep. 4, 2024", 6 pgs.
"European Application Serial No. 22747157.0, Communication Pursuant to Article 94(3) EPC mailed Nov. 26, 2024", 8 pgs.

* cited by examiner

INDEPENDENTLY IMPLANTABLE SENSORS FOR ORTHOPEDIC IMPLANTS

CLAIM OF PRIORITY

This application claims the benefit of U.S. Provisional Patent Application Ser. No. 63/197,094, filed on Jun. 4, 2021, the benefit of priority of which is claimed hereby, and which is incorporated by reference herein in its entirety.

TECHNICAL FIELD

The present disclosure is directed to systems, devices and methods incorporating sensors for use in performing, monitoring and evaluating medical procedures, such as arthroplasty procedures.

BACKGROUND

Arthroplasty procedures involve the implantation of medical devices, e.g., orthopedic implants, into anatomy of a patient. Typically, once the medical device is implanted into the patient, or even while it is being implanted, it is difficult to obtain feedback regarding the effectiveness of the implant or the implant procedure. Attempts have been made to obtain data from orthopedic implants using sensors.

U.S. Pat. No. 10,492,686 to Hunber et al. is titled "Devices, systems and methods for using and monitoring medical devices."

U.S. Pat. No. 10,531,826 to Wasielewske et al. is titled "Smart joint implant sensors."

OVERVIEW

The present inventors have recognized, among other things, that problems to be solved with traditional orthopedic implant sensor systems involve the necessity to customize implants to accommodate the sensor. As such, previously designed implants that have been carefully designed to provide load support and that have been approved by regulatory bodies must be redesigned. Furthermore, the ability to incorporate different sensing capabilities into the orthopedic implant is not readily accomplished when the implant and sensor are incorporated together as a packaged system.

The present inventors have also recognized, among other things, that problems to be solved with previous sensor systems for orthopedic implants involve incomplete sensor data, short battery life, infrequent data collection and other deficiencies.

The present subject matter can provide a solution to these and other problems, such as by providing sensor modules for use with orthopedic implants without requiring a redesign of existing orthopedic implants. The sensor modules can be configured to be coupled to anatomy in close proximity to the orthopedic implant device uncoupled from the orthopedic implant, thereby not interfering with existing device designs. Furthermore, the sensor module can be fabricated in a universally applicable housing that can be used with multiple orthopedic implant designs, and that can be adapted for use in different anatomies by coupling with attachment devices having different form factors, such as different exterior form factors but the same shaped socket for receiving the sensor modules.

In an example, a surgical sensor system for collecting internal patient data comprises a sensor module comprising a housing and a sensor disposed within the housing, and an attachment device comprising a socket for receiving the housing and an exterior anchor feature for attaching the attachment device to biological matter.

In an additional example, a method of implanting a sensor module for use with an orthopedic implant device comprises making an insertion portal in anatomy of a patient, positioning a sensor module in the anatomy in a first position relative to the insertion portal, and positioning an orthopedic implant in the anatomy in a second position relative to the insertion portal such that the orthopedic implant is separate from the sensor module.

In another example, a method of remotely interacting with a sensor implanted in anatomy independent of a co-implanted orthopedic device can comprise establishing a communication link with a sensor module implanted in the anatomy at a first position spaced apart from a second position where an orthopedic device is implanted, engaging the sensor with a surrounding environment of the orthopedic device in the anatomy, transmitting a signal related to a parameter of the surrounding environment from the sensor module via the communication link, receiving the signal at an interrogation device and displaying indicia of the parameter on a graphical user interface.

DETAILED DESCRIPTION

Figure 1:
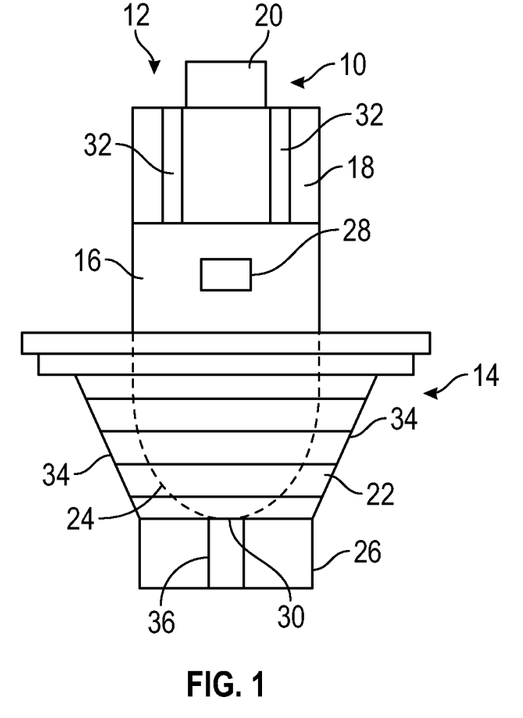
FIG. 1 is a side view of a sensor system that is independently implantable into anatomy of a patient for use in medical applications.

FIG. 1 is a side view of sensor system or assembly 10 that can be independently implantable into anatomy of a patient in medical applications, such as arthroplasty procedures. Sensor system 10 can comprise sensor module 12 and attachment device 14. Sensor module 12 can comprise housing 16, interface portion 18 and fastener portion 20. Attachment device 14 can comprise body 22 having socket 24 for receiving sensor module 12 and exterior 26.

Sensor module 12 can comprise a self-contained sensing unit configured to put one or more of various sensors in contact with or in proximity to various anatomic features and medical devices implanted in or at the anatomic features. Attachment device 14 can comprise an anchor device comprising a body to which sensor module 12 can be coupled to facilitate anchoring of sensor module 12 with the anatomic features in proximity to the implanted medical device. For example, different instances of attachment device 14 can have different exterior form factor for mating with different anatomies, such as a long bone or scapula, but can have similarly shaped sockets to receive the same sensor module 12. As such, sensor module 12 can be independent of the medical device such that the medical device need not be adapted or modified to accommodate a sensor. Thus, sensor system 10 can be used in conjunction with multiple varieties of medical devices without each medical device being reconfigured from a baseline, sensor-less version.

Housing 16 can comprise a body in which components of sensor module 12 can be located. In examples, housing 16 can be sealed to prevent liquid or biological matter from entering the interior of housing 16. Housing 16 can include side port 28 and distal port 30 that can comprise interfaces with surrounding tissue, biological matter or a medical device. Side port 28 can comprise a bore or hole that allows fluid to penetrate housing 16 to engage a component of a sensor engaged with side port 28 from an interior of housing 16 (e.g., in order to maintain a sealed interface). Side port 28 can comprise an electrode or interface component of a sensor that is extended into side port 28 to engage with the surrounding environment of housing 16. Distal port 30 can comprise a bore or hole to allow one or more of a lead, wire, antenna and the like to exit housing 16 to interact with a distal location, such as the exterior of a patient. In examples, housing 16 can be fabricated from polymer or plastic material or metal materials such as stainless steel. In examples, housing 16 can have a diameter in the range of approximately 10-12 mm and can have a length in the range of approximately 30-40 mm.

Interface portion 18 can comprise a portion of housing 16 configured to facilitate engagement with tissue. In examples, interface portion 18 can comprise porous material into which bone can grow. The porous material can be a coating applied to the exterior of housing 16. In examples, interface portion 18 can include ribs 32. Fastener portion 20 can comprise a feature to facilitate insertion and implantation of sensor system 10 via interaction with an instrument. Fastener portion 20 can be located at a proximal end of housing 16. For example, fastener portion 20 can comprise a structural feature to allow an insertion tool to attach to housing 16 or to facilitate an insertion tool rotating or driving housing 16. In examples, fastener portion 20 can comprise a threaded shaft or a hex head to which an elongate insertion tool can be coupled. In examples, sensor module 12 can include a sensor lead (not visible in FIG. 1; see lead 128 in FIG. 4) positioned, for example, at the distal end of housing 16.

Attachment device 14 can comprise body 22 configured to receive housing 16 to facilitate coupling of housing 16 to anatomy. Body 22 can transform or shape the outer perimeter shape or form factor of sensor system 10 to better mate with anatomy into which sensor system 10 is inserted into. In the illustrated example, attachment device 14 can comprise an external form factor of a cone-shaped body having a shaped outer surface 26 to facilitate engagement with an intramedullary canal of a long bone. In examples, outer surface 26 can comprise threads 34 that can facilitate screwing of body 22 into bone. In examples, outer surface 26 can comprise corrugations or porous structure. Threads, porous structure and corrugations can facilitate engagement with tissue, such as cortical bone. The cone shape, V-shape or tapered nature of outer surface 26 can facilitate engagement with intramedullary canals of long bones and other tissue. Body 22 can have other shapes to fit with other anatomical features, such as a spherical shape, a cylindrical shape, a disk shape, a cup shape and others to mate with other anatomic features of different sized intramedullary canals. As such, a surgeon can select the type of attachment device 14 to use with specific anatomic features or patients. The distal portion of body 22 can include lead port 36, which can comprise a passage through body 22 to allow access to a sensor lead positioned on or extending from housing 16. In examples, attachment device 14 can be fabricated from PEEK or polymer material. In additional examples, attachment device 14 can be fabricated from metal materials, such as stainless steel or trabecular metal.

Figure 2:
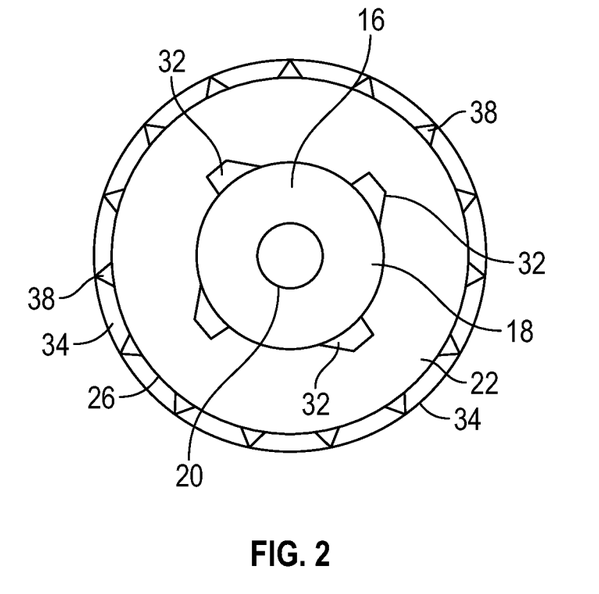
FIG. 2 is a top view of the sensor system of FIG. 1 showing a sensor module and an attachment device configured to engage the sensor module with anatomical features.

FIG. 2 is a top view of sensor system 10 of FIG. 1 showing sensor module 12 seated in attachment device 14. Sensor module 12 can comprise fastener portion 20, housing 16, interface portion 18 and ribs 32. Attachment device 14 can comprise body 22, outer surface 26, threads 34 and protrusions 38.

As can be seen in FIG. 2, outer surface 26 of attachment device 14 can be larger than the outer perimeter of sensor module 12. As such, attachment device 14 can change the overall form factor of sensor module 12. Sensor module 12 can comprise an easily manufactured shape such as a cylindrical or capsule shape. Housing 16 can thus have symmetry to improve manufacturability. Attachment device 14 can, however, have a customized or irregularly shaped geometry to mate with particular anatomic features. Socket 24 (FIG. 1) can have the same shape in each instance or configuration to mate with any housing of sensor module 12. As discussed below with reference to FIG. 6, sensor module 12 can be configured to have different electronic components, e.g., sensing capabilities. With housing 16 and socket 24 having mating shapes, any sensor module 13 can be used with any attachment device 14.

Attachment device 14 can further include features to facilitate anchoring with tissue. Because sensor system 10 can be implanted in anatomy separate from a medical device, it is important for sensor system 10 to be immobilized to maintain a spatial relationship with the medical device. Such immobilization can improve the consistency of data collected by sensor module 12 relative to the area of importance, e.g., the desired temperature, force or electrical parameter, as discussed below in greater detail.

Threads 34 can comprise features for facilitating insertion of attachment device 14 into tissue. For example, threads 34 can provide a mechanical advantage in advancing attachment device 14 axially into an intramedullary canal of a long bone while purchasing radial engagement. Protrusions 38 can comprise fixation features that project outward to prevent threads 34 from backing out of the tissue into which they have been inserted. As such, protrusions 38 can be located proximate only one end of body 22 to allow threads 34 to operate before protrusions 38 engage bone or tissue.

As discussed below, sensor system 10 can be configured to be used in conjunction with an orthopedic implant or another medical device. Sensor system 10 can be configured to work within the environment of the orthopedic implant to provide generate data and provide feedback relating to the orthopedic device or what the orthopedic device is experiencing. Thus, sensor system 10 can be placed nearby, immediately next to or in contact with the orthopedic implant to experience the same or similar environment as the orthopedic implant. However, sensor system 10 can be unattached, uncoupled or separate from the orthopedic implant such that the orthopedic implant need not be modified or adapted for specific use with or coupling, e.g., fastening, to sensor system 10.

Figure 3:
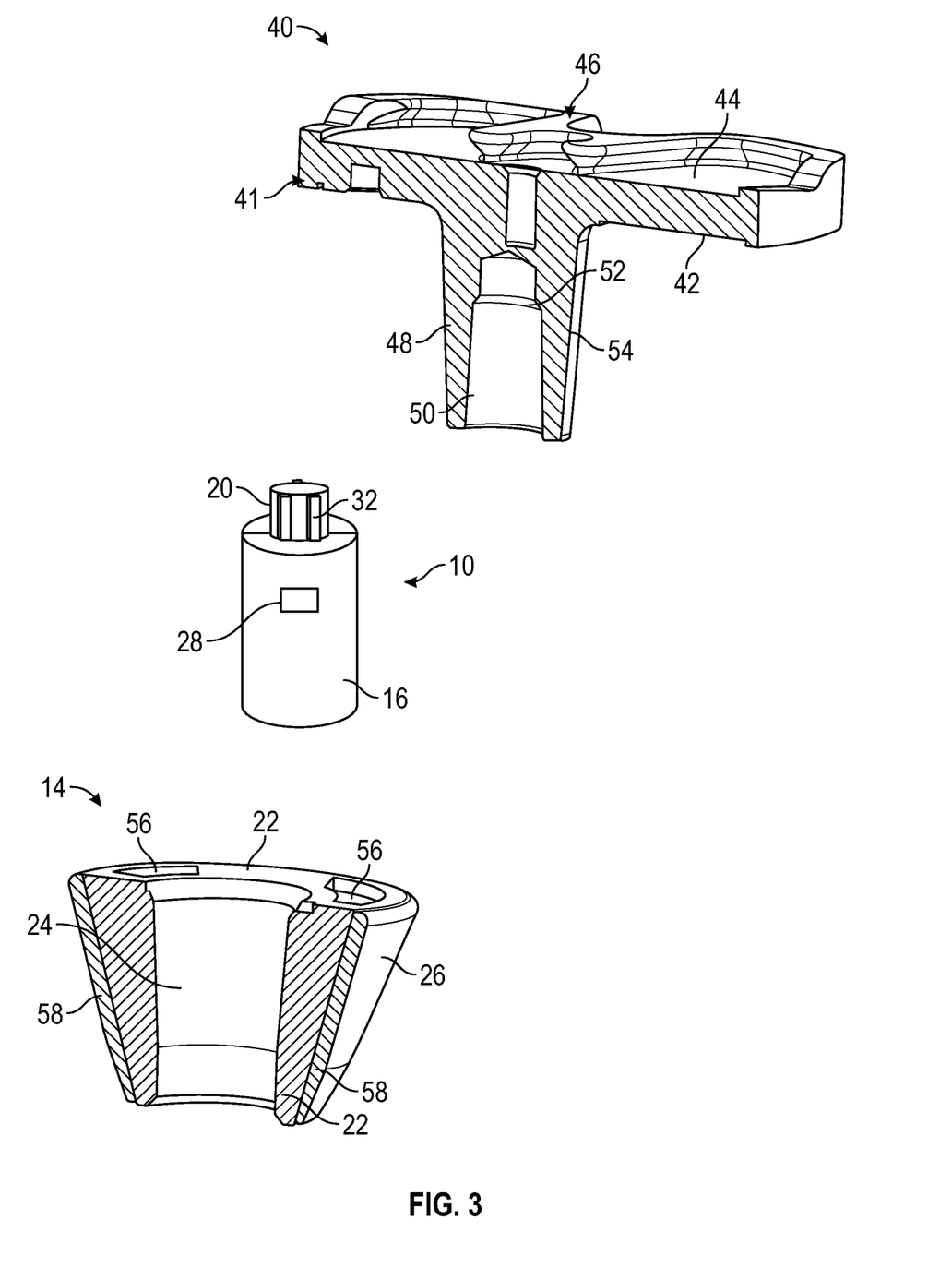
FIG. 3 is an exploded partial cross-sectional view of a tibial implant and the sensor system of FIG. 1.

FIG. 3 is an exploded perspective view of sensor system 10 positioned relative to tibial component 40. Tibial component 40 can comprise tibial tray 41 comprising bone-facing surface 42, bearing surface 44, retaining features 46, stem housing 48 and stem housing socket 50.

Figure 4:
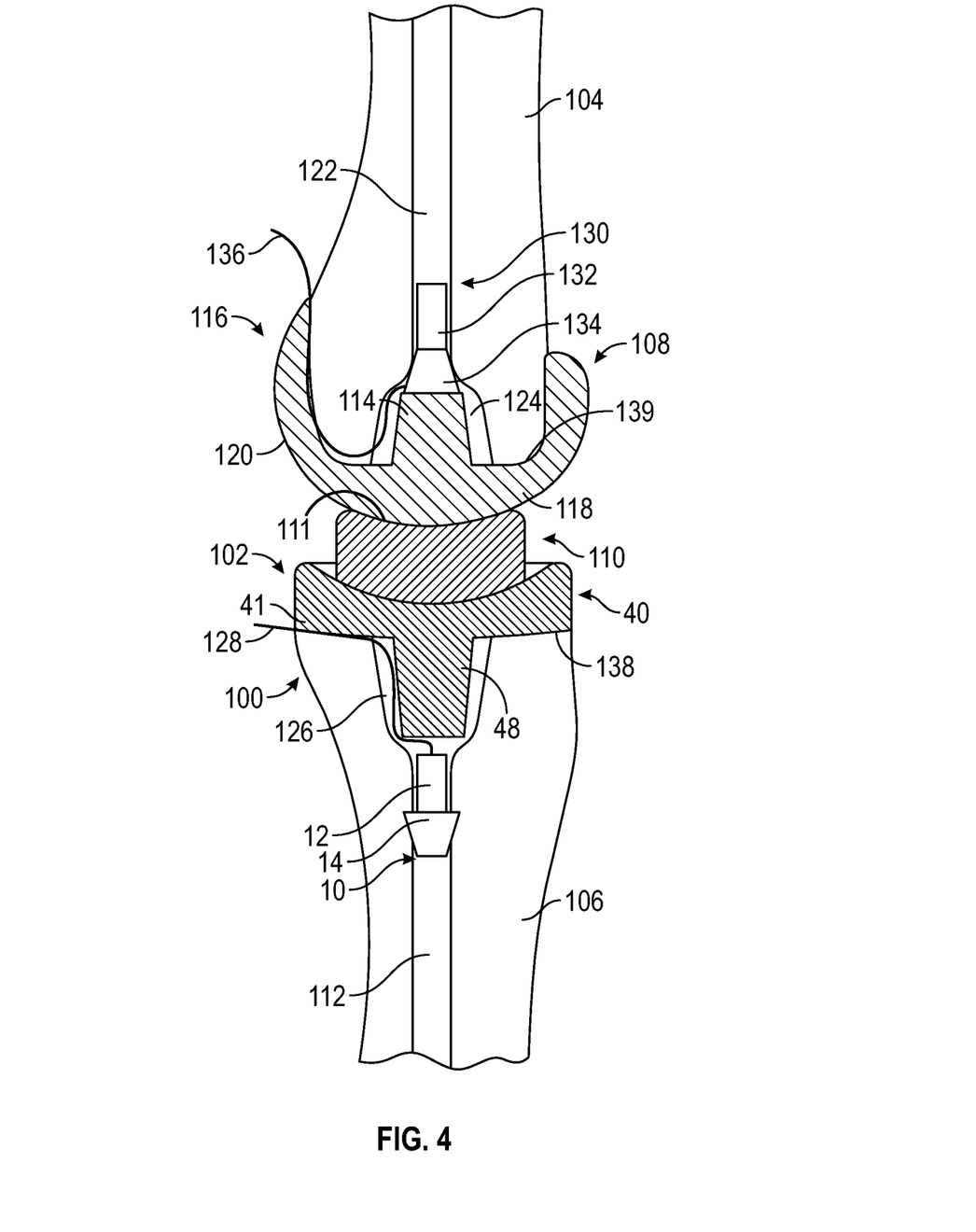
FIG. 4 is a schematic cross-sectional view of a knee joint showing a femur and a tibia each having a sensor system of the present disclosure.

A tibial stem (not shown) can be attached to tibial component 40 at socket 50. Stem housing socket 50 can include lip 52 that can engage a head of a lockdown post on a tibial stem to hold the tibial stem is place. Outer surface 54 of stem housing can be configured to be inserted into an intramedullary canal of a long bone such as a tibia. Retaining features 46 can be used to secure various bearing components against bearing surface 44 of tibial component 40 to engage a femoral component, as shown in FIG. 4. For example, retaining features 46 can include flanges having lips into which mating components of mobile or fixed bearings can be fitted to engage condylar surfaces of a femoral component. A tibial stem can be pushed down into an intramedullary canal of a tibia bone to anchor tibial component 40 so that bone-facing surface 42 contacts a resected bone surface of the tibia. Stem housing 48 can be inserted along the axis of the long bone into cancellous bone such that outer surface 54 can engage cortical bone.

Before tibial component 40 is positioned within the tibia bone, sensor module 12 and attachment device 14 can be inserted into the intramedullary canal. Housing 16 can be inserted into socket 24 to couple sensor module 12 and attachment device 14. Outer surface 26 can be engaged with cortical bone to hold sensor module 12 distal of tibial component 40. Attachment device 14 is shown in FIG. 3 with different features as compared to FIGS. 1 and 2. Socket 24 can be cylindrical shaped with open proximal and distal ends to allow sensor module 12 to be inserted from either direction and to allow components, e.g., electrodes or leads, can be allowed to interact with the environment of sensor module 12. Outer surface 26 can additionally be smooth or non-threaded or non-corrugated to, among other things, allow attachment device to slide more freely against tissue. In examples, body 22 can include other features to facilitate anchoring with bone or tissue. For example, body 22 can include depressions 56 to facilitate engagement with tissue or bone cement. Body 22 can additionally include coating 58, such as a porous coating or a roughened coating, to facilitate bone growth or immobilization.

In examples, sensor module 12 can be configured to be inserted at least partially into stem socket 50. As such, sensor module 12 can make use of an existing opening or receptacle in an implant. Housing 16 can be configured to have an interference fit with socket 50. However, sensor module 12 can additionally be configured to maintain independent anchoring to tissue and bone, such as via attachment device 14.

Sensor system 10 is illustrated in FIG. 3 as being used in conjunction with a tibial component. However, as discussed herein, sensor system 10 can be used with a variety of different implants, including femoral components, as shown in FIG. 4. Additionally, sensor system 10 can be used in shoulder joint arthroplasty in humerus and scapula bones, in hip joint arthroplasty in femur and pelvic bones, in ankle joint arthroplasty in tibia and talus bones and other procedures, orthopedic or otherwise.

FIG. 4 is a side cross-sectional view of knee joint 100 having total knee prosthetic 102 ("knee prosthetic 102") implanted in femur 104 and tibia 106. Tibia 106 can have sensor system 10 implanted therein and femur 104 can have sensor system 130 implanted therein. Sensor system 10 can comprise sensor module 12 and attachment device 14. Sensor system 130 can comprise sensor module 132 and attachment device 134.

Knee prosthetic 102 can comprise femoral component 108 and tibial component 40. Tibial component 40 can be coupled to a proximal end of tibia 106 and femoral component 108 can be coupled to a distal end of femur 104. Articulation component 110 can be positioned between tibial component 40 and the femoral component 108 to provide a low-friction articulation surface 111 for sliding motion between tibial component 40 and femoral component 108.

Tibial component 40 can comprise stem housing 48 and tray 41, also sometimes referred to as a tibial platform or tibial baseplate. Stem housing, or anchor, 48 can be implanted into tibia 106, for example, extending into intramedullary canal 112 of tibia 106. Stem housing 48 can provide a surface or surfaces for coupling or attachment between tibial component 40 and tibia 106. Although not shown, a stem extension can be coupled to stem housing 48 for extending further into intramedullary canal 112. Tray 41 can provide support for articulation component 110, such as within a cup or depression within tray 41. Articulation component 110 can be fastened to tibial component 40, such as with retaining features 46 (FIG. 3).

Femoral component 108 can comprise stem 114 and condyle portion 116 comprising generally convexly-curved anterior condyle surface 118 and posterior condyle surface 120. Stem, or anchor, 114 can be implanted into femur 104, for example, extending into intramedullary canal 122 of femur 104. Stem 114 can provide a surface or surfaces for coupling or attachment between femoral component 116 and femur 104. Although not shown, a stem extension can be coupled to stem 114 for extending further into intramedullary canal 122. Condyle surfaces 118 and 120 can interact with articulation surface 111 in order to provide a sliding relationship between femoral component 108 and articulation component 110, and in turn with tibial component 40 in order to simulate a natural knee joint (e.g., knee joint 100).

Femoral component 108 and tibial component 40 can be fabricated of typical materials for prosthetic implants, such as titanium or stainless steel. Such materials can be hard and as such are desirable to reduce wear and prevent damage or corrosion. However, such hard materials can be significantly harder than the bone material to which they are attached. As such, there is the potential for femoral component 108 and tibial component 40 to damage femur 104 and tibia 106, particularly during the implant procedures. To implant femoral component 108, intramedullary canal 122 can be reamed to produce cavity 124 to receive stem 114. Cavity 124 can be produced to be slightly smaller than stem 114 in order to obtain a tight fit so that femoral component 108 is not loose and likely to shift position. Likewise, to implant tibial component 40, intramedullary canal 112 can be reamed to produce cavity 126 to receive housing 48. Cavity 126 can be produced to be slightly smaller than housing 48 in order to obtain a tight fit so that tibial component 40 is not loose and likely to shift position. Thus, in order to implant and fully seat femoral component 108 and tibial component 40, it can be useful to impact each of femoral component 108 and tibial component 40 with a force to overcome resistance of the bone. Examples of devices for delivering such force include hammers, mallets and other impact devices. However, such force can potentially cause unintended modification of femur 104 and tibia 106. For example, femur 104 and tibia 106 can become cracked or damage if impacted by too high of a force, such as one that exceeds the stress limitations of the bone. Areas of a bone that have density lower than healthy bone can be especially susceptible to damage, particularly when the surgeon is unaware of bone at the impact site being weaker than normal.

In order to evaluate the implantation procedure of femoral component 108 and tibial component 40, as well as to monitor the performance and effectiveness of femoral component 108 and tibial component 40 after implantation, sensor systems 10 and 130 can be implanted into femur 104 and tibia 106 to, among other things, provide real-time or near real-time feedback of impaction forces on tibia 106 and femur 104. After the implantation procedure, sensor system 10 and 130 can remain in the patient, closed up within the anatomy, to provide feedback as to how 100 knee prosthetic 102 is performing and to evaluate loading of prosthetic 102 by the patient. Furthermore, sensor system 30 and 130 can be outfitted with additional capabilities, such as sensor capabilities, to provide further feedback and intervention or treatment.

Sensor module 12 can be assembled with attachment device 14. Attachment device 14 can be pushed down into canal 112. With reference to the orientation of FIG. 4, the narrow, distal end of attachment device 14 can be pushed distally into canal 112. As such, the wide, proximal end of attachment device 14 can resist proximal movement of attachment device 14. Attachment device 14 can be pushed sufficiently down into canal 112 to allow space for housing 16 to be spaced from tibial component 40. However, attachment device 14 can be positioned such that attachment device 14 and tibial component 40 can contact each other. Attachment device 14 and tibial component 40 can be left uncoupled, e.g., unfastened or unconnected. Lead 128 can be extended from sensor module 12 into cavity 126 and positioned between tibial tray 41 and the proximal resected surface 138 of tibia 106. Lead 128 can be used to extend the sensing capabilities of sensor module 12 beyond the confines of housing 16 to reach specific anatomic locations or a prosthetic device. If desired or needed based on an evaluation of tibia 106, a channel can be cut or scored in tibia 106 to accept lead 128 and allow tibial tray 41 to lie flush against surface 138.

Lead 128 can thus pass through an area, e.g., cavity 126, where bone cement can be used to affix tibial component 40. Lead 128 can be connected to a temperature sensor within sensor module 12 to sense the temperature of the bone cement to thereby monitor the cooling rate of the bone cement. As discussed below, lead 128 can additionally include wiring for other sensors and for a rechargeable battery. Sensor module 12 can additionally include an impact sensor, such as an accelerometer or a gyro-sensor, to sense impaction of tibial component 40 against tibia 106. Sensor module 12 can additionally include a sensor to sense an electrical parameter such as resistance, impedance, capacitance, phase angle and the like. Sensor module 12 can additionally include a pH sensor for analyzing tissue, such as determining the pH of synovial fluid.

Sensor module 132 can be assembled with attachment device 134. Attachment device 134 can be pushed up into canal 122. With reference to FIG. 3, the narrow, proximal end of attachment device 134 can be pushed proximally into canal 122. As such, the wide, distal end of attachment device 134 can resist distal movement of attachment device 134. Attachment device 134 can be pushed sufficiently up into canal 122 to allow femoral component 108 to engage resected surface 139. In examples, attachment device 134 can be positioned so that femoral component 108 contacts attachment device 134. However, attachment device 134 and femoral component 108 can be left uncoupled, e.g., unfastened or unconnected. Attachment device 134 can be positioned such that attachment device and femoral component 108 can be spaced apart. Lead 136 can be extended from sensor module 132 into cavity 124 and positioned between condyle surface 120 and the distal resected surface 139 of femur 104. If desired or needed based on an evaluation of femur 104, a channel can be cut or scored in femur 104 to accept lead 136 and allow femoral component 108 to lie flush against surface 139. Lead 136 can be constructed similar as lead 128 to include sensor electrodes and battery charging wires.

Sensor module 132 can comprise a temperature sensor, an impact sensor, an electrical parameter sensor and other sensors, as described below, to sense various parameters of femoral component 108. Sensor module 132 can be configured to sense bone cement temperature, impacts from an installation tool, pH of tissue, electrical parameters of tissue, as well as other parameters.

Sensor modules 12 and 132 can be configured to communicate with each other and an external interrogation device. For example, the position and orientation of each of tibial component 40 and femoral component 106 can be determined based on a common coordinate system. In examples, one of sensor modules 12 and 132 can be configured to communicate with an external device and another of sensor modules 12 and 132 can be configured to communicate with only the other sensor module. As such, coordinated orientation data can be communicated outside of the patient. Coordinated data regarding the motion of tibia 106 relative to femur 104 and vice versa can be used to, among other things, evaluate the range of motion of knee joint 100. As such, each of sensor modules 12 and 132 can include a motion sensor, such as a 3-axis accelerometer or magnetic Hall effect sensors and the like.

Figure 5:
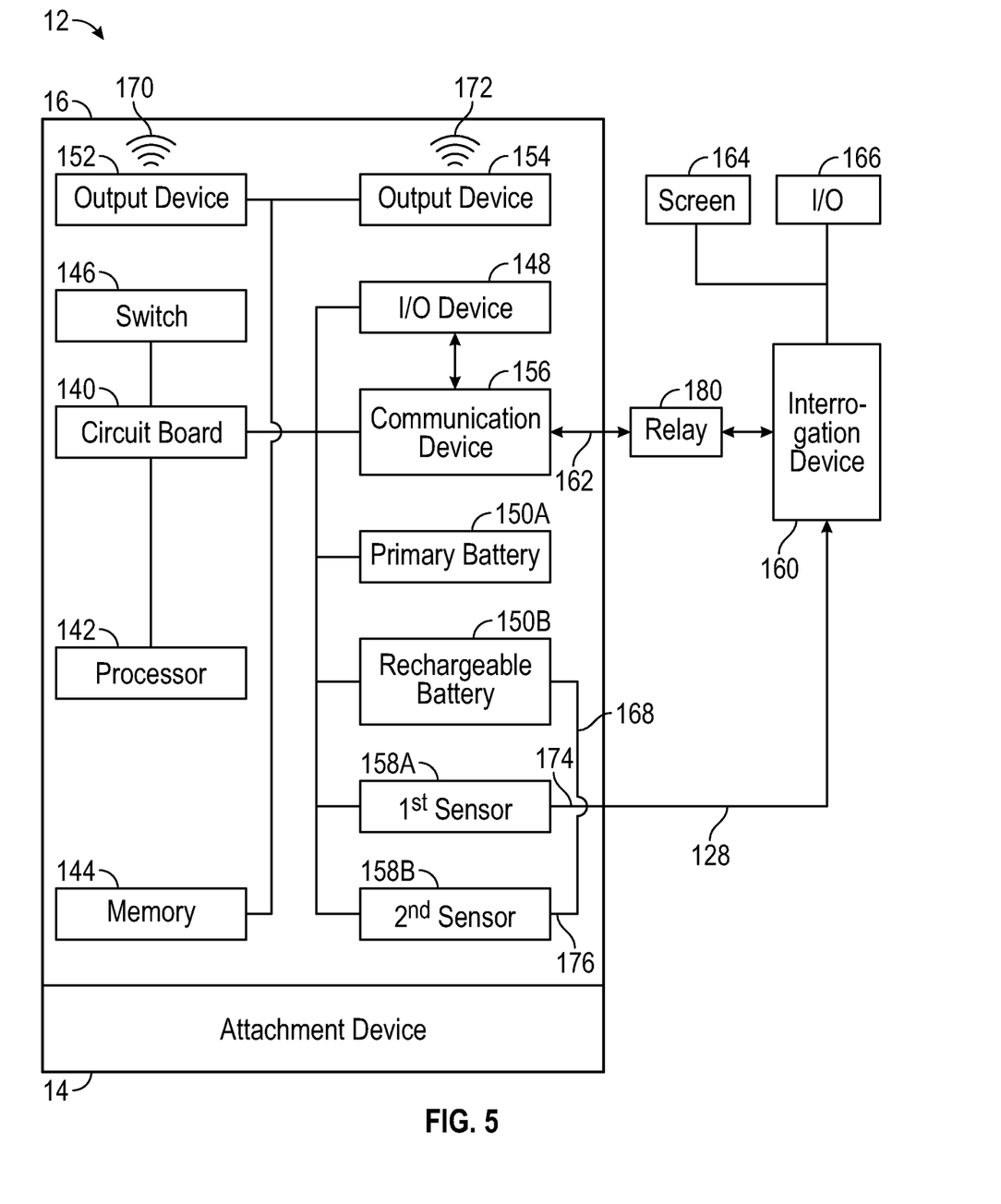
FIG. 5 is a schematic view of the sensor system including a sensor module and an attachment device suitable for use in the assemblies of FIGS. 1-4.

FIG. 5 is a block diagram illustrating components of sensor module 12. Although described with reference to sensor module 12, sensor module 130 can be configured similarly. Sensor module 12 can comprise housing 16, circuit board 140, processor 142, memory 144, switch 146, input/output (I/O) device 148, power source 150A, power source 150B, light source or output device 152, wave generator or output device 154, communication device 156, first sensor 158A and second sensor 158B. Housing 16 can be attached to or integral with attachment device 14. Sensor module 12 can be in communication with interrogation device 160.

Housing 16 can comprise a structural component to hold and support other components of sensor module 12. As described herein, because sensor module 12 can be uncoupled from a prosthetic implant configured to receive blows, e.g., loading, during implantation, housing 16 need not be configured robustly. In other words, housing 16 can be manufactured to contain elements of sensor module 12 without regard for withstanding increased loading from hammer blows. One result of such reduced structural requirements is the capability of making housing 16 from plastic materials that can be lighter and less expensive than metal materials. Housing 16 can be integral with attachment device 14. However, in other examples, housing 16 can be separate from attachment device 14 such that different attachment devices can be coupled to sensor module 12, as described herein. Housing 16 can be made of a medical grade plastic material, or can be made of other medical grade materials, such as stainless steel. Housing 16 can be made of a transparent or translucent material to facilitate transmission of light through housing 16 to improve visibility of any light sources disposed in or on housing 16, such as light source 152. Housing 16 can be sealed to keep the components therein dry and away from engagement with the environment of sensor module 12, except for those intended to engage tissue, such as lead 128 and side port 28.

Circuit board 140 can comprise a structural component for electrically and structurally coupling electrical components of sensor module 12. For example, circuit board 140 can comprise a silicon wafer or a chip onto which electrical couplings are attached for coupling switch 146, processor 142, memory 144, sensors 158A and 158B and the like.

Processor 142 can comprise an integrated circuit that controls operation of components of sensor module 12, such as I/O device 148, communication device 156 and sensors 158A and 158B. Processor can execute instructions stored in memory 144 to operate components of sensor module 12, such as sensors 158A and 158B.

Memory 144 can comprise any suitable storage device, such as non-volatile memory, magnetic memory, flash memory, volatile memory, programmable read-only memory and the like. Memory 144 can include instructions stored therein for processor 142 to control operation of sensor module 12. For example, memory 144 can include instructions for operating I/O device 148, communication device 156 and sensors 158A and 158B, as well as coordinating output from sensor module 12 and sensor module 132. Memory 144 can additionally include reference data for comparing data from sensors 158A and 158B, such as threshold conditions for when bone cement is cured or not cured or when rechargeable power source 150B is charged or not charged.

Switch 146 can comprise a an on/off switch for providing power from power sources 150A and 150B to sensors 158A and 158B, etc. Switch 146 can comprise an "alternate action" switch when transitioning between open or closed states. In alternate action switches, a switch can be flipped for continuous "on" or "off" operation. Switch 146 can comprise a toggle switch, a knife switch, a relay or a push-button switch. In examples, sensor module 12 does not include a switch and sensor module 12 can be powered on so long as one of primary power source 150A and rechargeable power source 150B is at least partially charged.

I/O device 148 can comprise one or more devices for receiving input from and sending output to a user of sensor module 12. In order to operate or obtain information from sensor module 12. I/O device 148 can comprise a button, a knob, a dial and the like. In examples, I/O device 148 can be omitted and sensor module 12 can communicate with interrogation device 160 in order to operate sensor module 12.

Communication device 156 can comprise one or more devices for receiving input from interrogation device 160 or providing an output to interrogation device 160 via various signals. Communication device 156 can provide signal 162 to interrogation device 160. Interrogation device 160 can thereafter, for example, display on human interface device 164, such as a video display monitor, an indication of information from sensor module 12. Interrogation device 160 can further comprise I/O device 166 to receiving input from and send output to a user of interrogation device 160, such as a surgeon.

Communication device 156 can receive signal 162 from interrogation device 160 for storing information on memory 144 or providing information to processor 142 for operating switch 146, sensors 158A and 158B, communication device 156, output devices 152 and 154 and other components of sensor module 12. In examples, communication device 156 can communicate using wireless communications signals, such as Bluetooth, WiFi, Zigbee, infrared (IR), near field communication (NFC), 3GPP or other technologies. In examples, communication device 156 can comprise a wired connection or can include a port for receiving a wire for a wired connection.

Communication device 156 can be used in conjunction with antenna relay 180. Antenna relay 180 can comprise an independently implantable component that can be located within tissue between sensor module 12 and the skin. Antenna relay 180 can be uncoupled from each of sensor module 12 and the orthopedic implant. As such, antenna relay 180 can comprise an intermediary to allow native communication capabilities of communication device 156 to be enhanced or relayed outside of the patient with a stronger signal. Antenna relay 180 can be energized with power from interrogation device 160 to receive and rebroadcast a signal from sensor module 12.

Power source 152A can comprise an energy storage device such as a battery including an electrochemical cell, such as an alkaline or zinc-manganese battery. In examples, power source 152A can comprise a primary, or non-rechargeable battery.

Power source 152B can comprise a rechargeable battery. Power source 152B can comprise lead 168. Lead 168 can provide a conductor for charging power source 152B. Power source 152B can additionally be configured for contactless charging, such as via induction charging.

Power sources 152A and 152B can be configured to provide power to different components of sensor module 12. Primary battery, or power source 152A can provide long term battery power and can provide power to low-frequency sensor operations over the lifetime of sensor module 12. Rechargeable batter, or power source 152B can provide short term battery power and can provide short duration, high frequency sensor operations, such as during exercise conducted as part of post-operative rehabilitation. Sensor module 12 can include one or more of each of power sources 152A and 152B.

Output device 152 can comprise one or more devices for producing light waves 170, such as incandescent light bulbs, light-emitting-diodes and the like. In examples, output device 152 can be configured for emitting different colors or wavelengths of light. Output device 152 can provide visual indications of when sensor module 12 is performing different functions, such as actively sensing. For example, output device 152 can be configured to emit orange, yellow and green light, so that an operator can confirm that different functions of sensor module 12 are being performed, or that a loss of communication or a malfunction of sensor module 12 is occurring.

Output device 154 can include or comprise a device such as for making wave 172, such as a sound wave or a vibration wave. In an example, output device 154 can comprise an auditory device, such as a speaker or amplifier for producing an auditory signal or sound to indicate that sensor module 12 is in communication with interrogation device 160. In other examples, output device 154 can comprise tactile device, such as a reciprocating or oscillating device, for producing a vibration that can be felt by a surgeon, operator of interrogation device 160 or patient. For example, wave 172 can communicate with a device worn by a surgeon at interrogation device 160 that can vibrate when receiving wave 172.

Sensors 158A and 158B can comprise a variety of different sensors, such as temperature, pH, force, vibration, impact, position, motion, capacitance, conductance, impedance and the like. Only one of sensors 158A and 158B can be included in sensor module 12 or more than two sensors can be included in sensor module 12. Sensors 158A and 158B can be modular, as described with reference to FIG. 6. Sensors 158A and 158B can include leads 174 and 176, respectively, that can be incorporated (e.g., co-extending) into lead 128. Leads 174 and 176 can provide for remote sensing capabilities outside of housing 16. Lead 128 can thus comprise a cable that is a bundle of other cables or wires relating to, among other things, power transmission, data transmission and signal transmission.

Sensor module 12 and the other sensor modules described herein can be disposable or can be reusable. In order to reduce the cost of manufacturing each sensor module 12 described herein, each can be configured as one-time-use items. Housing 16 can be separable from attachment device 14 so that each component can be cleaned. Housing 16 can include one or more seals to prevent biological fluid or cleaning fluid from reaching electrical components within housing 16. In examples, the various housings described herein can include separable sub-components or sub-housing such that the electrical component located therein can comprise a modular component. As such, sensor module 12 can be customized to include only the sensors and input and output devices that are desired for a particular procedure.

Figure 6:
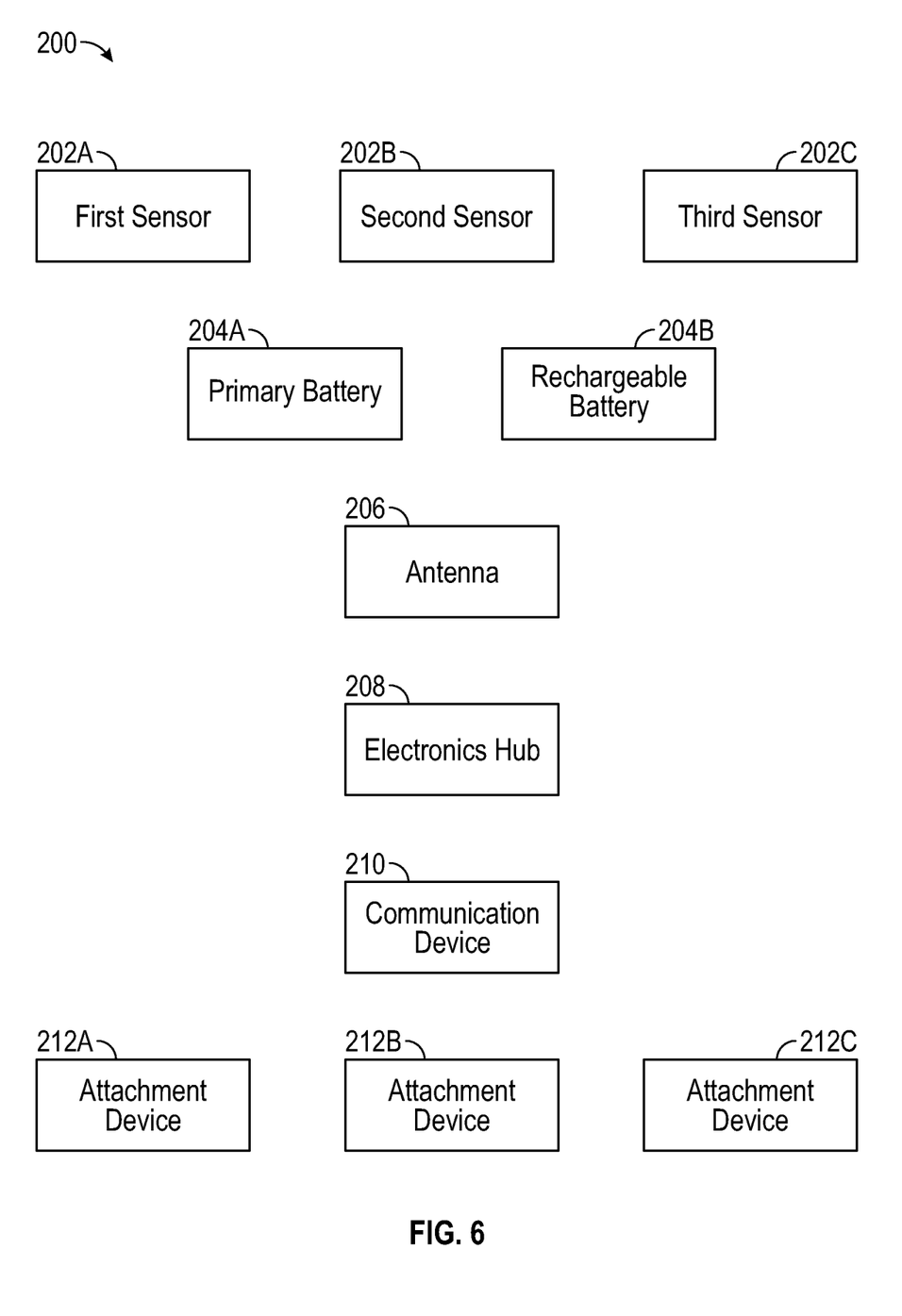
FIG. 6 is a schematic view of a sensor module configured to be assembled from a plurality of modular components.

FIG. 6 is a schematic view of sensor module 200 configured to be assembled from a plurality of modular components 202A-212C, amongst others. Sensor module 200 can be fabricated from one or more of first sensor 202A, second sensor 202B, third sensor 202C, primary batters 204A, rechargeable battery 204B, antenna 206, electronic hub 208, communication device 210, attachment device 212A, attachment device 212B and attachment device 212C. FIG. 6 is described with reference to exemplary modular components. However, any of the components described herein, such as the various elements of FIG. 5, can be configured as an independent modular component.

Each of modular components 202A-212C can comprise an independent component enclosed in a sealed housing. Each sealed housing can comprise first and second sets of ports for communicating with another modular component. The ports can be configured to communicate electrical signals, such as communication signals, data signals, power signals and the like. Ends of each modular component 202A-212C configured to abut an end of another of modular components 202A-212C can include one or more sealing elements configured to prevent fluid, e.g., biological of cleaning fluid, from entering between abutting modular components at the locations of such ports. Sealing components can comprise flanges or O-ring or closed loop seals made from a resilient material configured to compress between adjacent modules to prevent egress of fluid and biological material. Each of components 202A-212C can include an individual housing that together can form housing 16.

Electronic hub 208 can comprise components for allowing each of modular components 202A-212C to function together. Sensors 202A-202C can comprise various sensor modules desirable for use in surgical procedures. In examples, sensor 202A can comprise a temperature sensor, sensor 202B can comprise a force sensor and sensor 202C can comprise a pH sensor. These and other sensors can additionally comprise positions sensors, accelerometers, resistance sensors, capacitance sensors and the like.

The modular components of FIG. 6 can allow sensor module 12 and sensor module 130 to be custom built for particular applications. Thus, only the components needed for a particular procedure or patient can be incorporated therein. For example, a temperature sensor can be omitted if bone cement is not part of the operative plan for implanting the prosthetic device.

Figure 7:
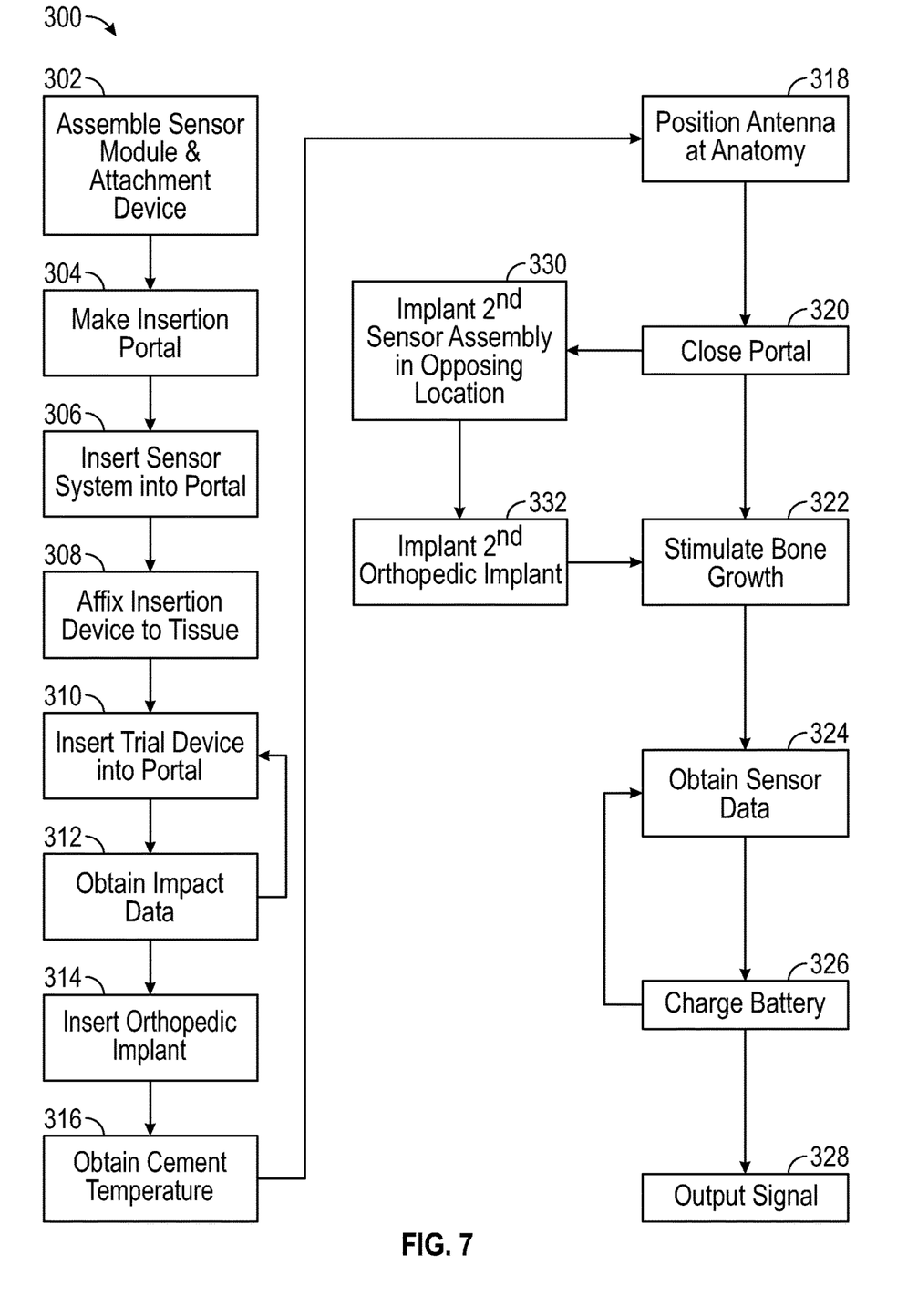
FIG. 7 is a schematic line diagram showing methods of implanting a sensor system and obtaining sensor data in conjunction with an orthopedic implant.

FIG. 7 is a schematic line diagram showing methods 300 of implanting sensor system 10 and obtaining sensor data in conjunction with orthopedic implant 40. Steps 302-326 are described with reference to sensor system 10, but can additionally be applicable to sensor system 130, with sensor system 10 being applicable to steps 330 and 332. Similarly, steps 302-332 are discussed with reference to a total knee arthroplasty, but can be applicable to acetabular cup implants in hip arthroplasty, humeral stem and glenoid components in total shoulder arthroplasty, humeral tray, glenoid baseplate and glenosphere components in reverse shoulder arthroplasty, and tibial and talar components in total ankle arthroplasty.

At step 302, sensor module 12 can be assembled with attachment device 14. Housing 16 can be seated in socket 24. In examples, housing 16 can be threaded or snap-fit into socket 24 to prevent disassembly. Attachment device 14 can be selected to have a shape of outer surface 26 that has a form factor or geometry to mate with and engage with the selected anatomic features for the procedure. For example, a tapered or cylindrical shaped attachment device 14 can be selected for mating with intramedullary canal 112 or 122.

At step 304, an insertion portal can be made in a patient. For example, incisions can be made in knee joint 100 (FIG. 4) to expose the proximal end of tibia 106 and the distal end of femur 104. Thereafter, the proximal end of tibia 106 can be resected to expose intramedullary canal 112 and the distal end of femur 104 can be resected to expose intramedullary canal 122. The insertion portal and resection for femur 104 can additionally be made at steps 330 and 332.

At step 306, sensor system 10 can be inserted into intramedullary canal 112 after being pushed through the insertion portal of tibia 106. After sensor system 10 is positioned within the anatomy, the sensor system can be activated to begin collecting data and outputting data to an external device.

At step 308, attachment device 14 can be engaged with tissue to immobilize sensor module 12. Attachment device 14 can be threaded into cortical bone, pushed into cancellous bone, inserted into soft tissue and the like. For example, threads 34 can be sliced into soft tissue or bone, protrusions 38 can be poked into soft tissue or bone. Attachment device 14 can be sufficiently immobilized so as to be eventually positioned in a fixed position relative to tibial component 40 in order to facilitate collection of consistent data.

At step 310, a tibial trial device can be inserted through the insertion portal and positioned in intramedullary canal 112. The tibial trial device can comprise one of a plurality of incrementally sized devices that allow the fit and size of a prosthetic implant to be selected as the finally implanted device. In order to fully seat the trial device, the trial device can be impacted with an impaction device, such as a mallet, a hammer, a weight and the like. A surgeon can manually operate the mallet or hammer to provide the desired force, typically based on feel or experience.

At step 312, impact data from sensor module 12 can be obtained. For example, sensor module 12 can sense vibration, acceleration and the like through tibia 106 from the tibial trial device in examples when sensor system 10 is configured to be spaced apart from the implant. The magnitude of the vibration or acceleration can be determined by a sensor within sensor module 12. Additionally, sensor module 12 can sense direct impact (e.g., vibration or acceleration) of the impact device through the tibial trial device in examples when sensor system 10 is configured to about the implant.

A communication device within sensor module 12 can transmit the vibration magnitude to interrogation device 160 (FIG. 5). Interrogation device 160 can have installed thereon software able to correlate the vibration data into a force impact reading. In additional examples, sensor module 12 can itself be configured to convert raw sensor data into a force impact reading for transmission to interrogation device 160. The surgeon can view the force impact reading on interrogation device 160 to determine if the tibial trial device has been impacted with sufficient force to fully seat the trial device without harming tibia 106. Thus, the surgeon can incrementally impact the tibial trial device with the mallet or hammer until the desired force level is reached. Interrogation device 160 can assist the surgeon determine if sufficient force or too much force has been delivered to the implant. For example, interrogation device 160 can provide visual or audio indicators of the level of force in a format to allow the surgeon to evaluate if too little, too much or an adequate amount of force has been delivered, such as yellow, red and green lights. In examples, interrogation device 160 can comprise a smartphone. Operation or complexity of sensor module 12 can be reduced by having interrogation device 160 perform operations of sensor module 12 when in communication. As such, some of the functions described herein as being performed by processor 142 and/or circuit board 140 can be performed by interrogation device 160. In examples, sensor module 12 can be configured to collect data and interrogation device 160 can be configured to collect and process data. In additional examples, sensor module 12 can be instructed to only collect data when directed to do so by interrogation deice 160.

In examples, steps 310 and 312 can be omitted and step 314 can be directly performed to implant the orthopedic implant device. The size and shape of the orthopedic implant device can be selected from a pre-operative surgical plan including patient imaging that can be updated based on intraoperative conditions.

At step 314, the selected orthopedic implant to match the fit ascertained with the trialing device can be implanted. Implantation of the selected orthopedic implant can be performed using sensor feedback as is described with reference to step 312. The selected orthopedic implant can be affixed to tibia 106 with bone cement.

At step 316, sensor module 12 can be used to obtain feedback regarding the implantation of tibial component 40. For example, bone cement used at step 314 can be formed intraoperatively from two constituent components, e.g., a liquid methyl methacrylate monomer and a powered MMA-styrene co-polymer. The constituent components can undergo an exothermic reaction to undergo a hardening process to interlock the bone and prosthetic device. The exothermic reaction can release heat, which can be an indication of the success of the two constituent components mixing together adequately, which can be an indication of the effectiveness of the bone cement to hold the prosthetic component in place. Thus, sensor module can provide an output of the magnitude of the temperature in the bone cement to allow monitoring of the curing process of the bone cement. The temperatures of the bone cement can be displayed on interrogation device 160 in a visual format to allow for evaluation by a surgeon. Interrogation device 160 or sensor module 12 can be provided with data relating to effective curing temperatures of various bone cements such that interrogation device 160 can assist the surgeon in determining if sufficient curing has occurred.

At step 318, an antenna can be extended from sensor module 12 to a desired location in the patient. In examples, the antenna can be extended along selected anatomy where it is desired for lead to engage with the environment of the orthopedic implant, such as where it is desired to obtain temperature or pH reading or where it is desirable to stimulate bone growth. In examples, the antenna can be extended out of the knee joint prior to step 316 and the application of bone cement and the complete insertion of the orthopedic implant. An antenna, such as lead 128, can extend from housing 16 to facilitate interaction with ex-vivo (extracorporeal) locations, e.g., locations outside of the insertion portals formed at step 304. As shown in FIG. 5, lead 128 can be made up of one or more strands of material extending from a battery, a sensor and a communication device. The antenna can be positioned at sub-dermal or sub-cutaneous locations to allow for better interaction with external devices, such as a charging station or an interrogation device, and to allow for better interaction with particular anatomy. In examples, sensor module 12 can be used in conjunction with a separately implanted antenna relay 180 wherein an antenna within housing 16 of sensor module 12 located deep within tissue can be pointed toward the relay antenna located just below the skin. Such leads, antennas and antenna relays can facilitate smaller sensor sizes and stronger output signals from sensor module 12.

At step 320, the insertion portal in tibia 106 into which tibial component 40 was inserted can be closed. As such, tibial component 40 can be enclosed within anatomy of the patient. Furthermore, sensor system 10 can additionally be enclosed within the anatomy of the patient. In examples, lead 128 can be positioned outside of the anatomy through the closed up insertion portal.

At step 322, sensor system 10 can be used to stimulate bone growth in the area of tibial component 40. For example, electrical current can be passed through lead 128 to stimulate bone growth. In examples, bone growth can be stimulated by directly flowing current through leads 128 and 136. Lead 128 can additionally be used as an electromagnetic current carrying coil. Lead 128 can be used to stimulate bone growth using the methods described in "Electrical Stimulation in Bone Healing: Critical Analysis by Evaluating Levels of Evidence" to Michelle Griffin and Ardeshir Bayat.

At step 324, sensor data can be obtained from sensor module 12. Data from any of the sensors referenced herein can be obtained if sensor module 12 is configured to sense such parameters. Such sensor data can be used to evaluate the effectiveness of tibial component 40. Additionally, sensor module 12 can be used to collect load data, e.g., forces applied to tibial component 40, during use by the patient. Sensor module 12 can collect real time data for transmission to interrogation device 160. Additionally, sensor module 12 can store historical data over a period of time that can later be downloaded by interrogation device 160 in a single step. In examples, sensor module 12 can be configured to sense the pH of synovial fluid in knee joint 100 to assess osteoarthritis.

At step 326, batteries within sensor module 12 can be charged. For example, rechargeable power source 150B can be positioned proximate a charging station such that power source 150B can be charged wirelessly through the skin, such as by inductance. In examples, interrogation device 160 can comprise recharging capabilities for rechargeable power source 150B. In examples, lead 128, which can incorporate lead 168 for rechargeable power source 150B, can be connected to, e.g., plugged into, the charging station. In additional examples, lead 128 can be positioned proximate, e.g., in contact with, a wireless charging station to provide, for example, inductive charging of rechargeable power source 150B.

Additionally, at step 326 or other points in time where interrogation device 160 is brought into communication with sensor module 12, software, firmware or other aspects of sensor module 12 can be updated or adjusted. For example, data collection and processing algorithms of sensor module 12 can be adjusted to be personalized for a patient profile. In examples, a movement profile for the patient in which sensor module 12 is implanted can be factored into a monitoring algorithm. Thus, more active patients could be monitored more frequently than less active patients. Additionally, data collection can be adjusted based on patient activity to preserve battery life. Sensor module 12 can also be configured to self-adjust based on sensed activity of the patient without the aid of interrogation device 160. Such personalization can be performed by interrogation device 160 by the patient, such as by using a smartphone. Sensor implant 12 can trigger to collect additional data for some patients and the increased or personalized monitoring could happen at the smartphone. However, for security purposes, updates can be performed locally, such as at a medical facility and can incorporate both security and upgrade assurance, i.e., if an upgrade fails, the previous implant software can still be re-installed. In additional examples, sensor module 12 can perform self-calibration measurements that can ensure correct local measures are being captured, accounting for environmental factors (e.g., temperature or altitude) or other deviations. As mentioned, sensor module 12 can, for example, self-adjust the frequency at which measurements are obtained based on user activity, the range of the magnitude of the sensor measurements. Furthermore, aspects of instability within sensor module 12 could be auto-stabilized by processor 142 and the like, such as to eliminate noise from the collected data.

At step 328, information and data obtained from sensor module 12 can be output in a format suitable for use. In examples, interrogation device can display textual or graphical information or indicia relating to sensor data on a display screen or graphical user interface of interrogation device 160 or another computing device. Visual, audio and tactile feedback can also be provided from interrogation device 160 or another computing device. In other examples, sensor module 12 can itself provide output in the form of graphical information, a light, a sound or a vibration.

Steps 324-328 can be repeated as often as necessary or desired to obtain feedback to evaluate performance of a prosthetic implant or healing and functioning of a joint.

Steps 330 and 332 can be performed to implant a second prosthetic implant in the patient that can function in conjunction with the first prosthetic implant of steps 302-320.

At step 330, sensor system 130 can be inserted into intramedullary canal 122 after being pushed through the insertion portal of femur 104. Likewise, attachment device 134 can be engaged with tissue to immobilize sensor module 132.

At step 332, a femoral trial device can be inserted through the insertion portal and positioned in intramedullary canal 122. Impact data from sensor module 132 can be obtained. An antenna, such as lead 136, can extend from a housing to facilitate interaction with extra-corporal locations, e.g., locations outside of the insertion portals previously formed. The insertion portal in femur 104 into which femoral component 108 was inserted can be closed. Furthermore, sensor system 130 can additionally be enclosed within the anatomy of the patient. In examples, lead 136 can be positioned outside of the anatomy.

Thus, at step 324, sensor system 130 can be used to stimulate bone growth in the area of femoral component 108. Sensor data can be obtained from sensor modules 12 and 132. For example, kinematic data can be collected regarding the movement of tibial component 40 or femoral component 108 relative to knee joint 100. At step 326, one or more batteries within sensor module 130 can be charged.

The systems, devices and methods discussed in the present application can be useful in efficiently and inexpensively implanting sensing capabilities into a patient in conjunction with an orthopedic implant. A modular and generic sensing module can be coupled with an attachment device that can be adapted for use with different anatomies. The assembly of the generic sensor modular and anatomy-specific attachment device can be implanted in a patient in close proximity to or in contact with an orthopedic implant to sense the anatomic environment of the orthopedic implant. The sensing module can, however, not require any special features on the orthopedic implant to allow for interaction with the orthopedic implant or its surroundings. The sensing module can, therefore, be particularly adapted for sensing, power capabilities and communication capabilities without, or with less, regard to the orthopedic implant. For example, the sensor module need not be robust to survive impacts and wear and tear from articulation of the joint, and the sensor module can be increased in size from a sensor module needing to be impregnated in an orthopedic device. The sensor module can therefore include robust power capabilities and can include extension devices (e.g., a lead or an antenna relay) to allow for better ex-vivo interaction.

EXAMPLES

Example 1 is a surgical sensor system for collecting internal patient data, the system comprising: a sensor module comprising: a housing; and a sensor disposed within the housing; and an attachment device comprising: a socket for receiving the housing; and an exterior anchor feature for attaching the attachment device to biological matter.

In Example 2, the subject matter of Example 1 optionally includes wherein the sensor comprises a temperature sensor.

In Example 3, the subject matter of any one or more of Examples 1-2 optionally include wherein the sensor comprises a pH sensor.

In Example 4, the subject matter of any one or more of Examples 1-3 optionally include wherein the sensor is configured to sense an electrical parameter.

In Example 5, the subject matter of any one or more of Examples 1-4 optionally include wherein the sensor module further comprises: a communication device located within the housing and in electronic communication with the sensor, the communication device configured to transmit data collected by the sensor outside the housing.

In Example 6, the subject matter of Example 5 optionally includes wherein the communication device comprises a wireless communication device.

In Example 7, the subject matter of any one or more of Examples 5-6 optionally include wherein the sensor module further comprises: a lead connected to the sensor and extending out of an exterior of the housing.

In Example 8, the subject matter of Example 7 optionally includes a rechargeable battery.

In Example 9, the subject matter of Example 8 optionally includes a primary battery.

In Example 10, the subject matter of any one or more of Examples 8-9 optionally include wherein the lead comprises a recharging cable for the rechargeable battery.

In Example 11, the subject matter of Example 10 optionally includes wherein the attachment device further comprises: a sensor lead port extending from the socket to an exterior wall of the attachment device.

In Example 12, the subject matter of any one or more of Examples 1-11 optionally include wherein the sensor module further comprises: a porous structure disposed outside the housing, the porous structure configured to promote bone ingrowth to the housing.

In Example 13, the subject matter of any one or more of Examples 1-12 optionally include wherein the sensor module further comprises: an instrument feature configured to engage an insertion tool.

In Example 14, the subject matter of Example 13 optionally includes wherein the instrument feature comprises a threaded shaft located on a proximal portion of the housing or a hex head located on a proximal portion of the housing.

In Example 15, the subject matter of any one or more of Examples 1-14 optionally include wherein the sensor module further comprises a plurality of fixation features on an exterior of the housing.

In Example 16, the subject matter of Example 15 optionally includes wherein the plurality of fixation features comprises elongate ribs.

In Example 17, the subject matter of any one or more of Examples 1-16 optionally include wherein the exterior anchor feature comprises: threading extending around the anchor device.

In Example 18, the subject matter of any one or more of Examples 1-17 optionally include wherein the exterior anchor feature comprises: projections extending from an exterior wall of the anchor device.

In Example 19, the subject matter of any one or more of Examples 1-18 optionally include wherein the anchor feature comprises a tapered body configured to engage an intramedullary canal of a bone.

In Example 20, the subject matter of any one or more of Examples 1-19 optionally include wherein the attachment device is fabricated from PEEK or polyethylene.

In Example 21, the subject matter of any one or more of Examples 1-20 optionally include an antenna relay separately implantable from the sensor module.

Example 1 is a method of implanting a sensor module for use with an orthopedic implant device, the method comprising: making an insertion portal in anatomy of a patient; positioning a first sensor module in the anatomy in a first position relative to the insertion portal; and positioning an orthopedic implant in the anatomy in a second position relative to the insertion portal such that the orthopedic implant is separate from the sensor module.

In Example 2, the subject matter of Example 1 optionally includes collecting output from the first sensor module during a procedure.

In Example 3, the subject matter of Example 2 optionally includes wherein the sensor output comprises vibration data.

In Example 4, the subject matter of Example 3 optionally includes using the output of the first sensor module to determine a force impacted on the orthopedic implant, a trial implant or an instrument.

In Example 5, the subject matter of any one or more of Examples 2-4 optionally include wherein the sensor output comprises temperature data.

In Example 6, the subject matter of Example 5 optionally includes using the output of the first sensor module to determine a temperature of bone cement applied to the orthopedic implant in order to monitor curing of the bone cement.

In Example 7, the subject matter of any one or more of Examples 1-6 optionally include coupling the first sensor module with an attachment device configured to engage with anatomical structures.

In Example 8, the subject matter of Example 7 optionally includes engaging the attachment device with cortical bone of the anatomical structures.

In Example 9, the subject matter of any one or more of Examples 7-8 optionally include engaging threading or protrusions of the attachment device with the anatomical structure.

In Example 10, the subject matter of any one or more of Examples 1-9 optionally include extending a lead from the first sensor module through skin of the patient.

In Example 11, the subject matter of Example 10 optionally includes conducting electricity through the lead to stimulate bone growth at the anatomy.

In Example 12, the subject matter of any one or more of Examples 10-11 optionally include charging a battery of the first sensor module using the lead.

In Example 13, the subject matter of any one or more of Examples 1-12 optionally include implanting a second sensor module in a bone of a joint on an opposite side of the joint as the first sensor module.

In Example 14, the subject matter of Example 13 optionally includes analyzing range of motion data for a joint of the anatomy using position data from the second sensor module and the first sensor module.

In Example 15, the subject matter of any one or more of Examples 1-14 optionally include wherein the sensor module contacts the orthopedic implant.

In Example 16, the subject matter of any one or more of Examples 1-15 optionally include communicating with the first sensor module through an antenna relay implanted in the anatomy separate from the first sensor module and the orthopedic implant.

Example 1 is a method of remotely interacting with a sensor implanted in anatomy independent of a co-implanted orthopedic device, the method comprising: establishing a communication link with a sensor module implanted in the anatomy at a first position spaced apart from a second position where an orthopedic device is implanted; engaging the sensor with a surrounding environment of the orthopedic device in the anatomy; transmitting a signal related to a parameter of the surrounding environment from the sensor module via the communication link; receiving the signal at an interrogation device; and displaying indicia of the parameter on a graphical user interface.

In Example 2, the subject matter of Example 1 optionally includes wherein: the surrounding environment of the orthopedic device comprises bone cement; and the signal comprises temperature of the bone cement.

In Example 3, the subject matter of any one or more of Examples 1-2 optionally include wherein: the surrounding environment of the orthopedic device comprises synovial fluid; and the signal comprises a pH level of the synovial fluid.

In Example 4, the subject matter of any one or more of Examples 1-3 optionally include wherein: the surrounding environment of the orthopedic device comprises bone; and the signal comprises a force transmitted through the bone.

In Example 5, the subject matter of any one or more of Examples 1-4 optionally include wherein: the surrounding environment of the orthopedic device comprises bone; and the signal comprises an electrical current to stimulate growth of the bone.

In Example 6, the subject matter of any one or more of Examples 1-5 optionally include engaging the sensor with the surrounding environment of the orthopedic device using a lead cable extending from the sensor module.

In Example 7, the subject matter of Example 6 optionally includes recharging a battery of the sensor module through the lead cable.

In Example 8, the subject matter of any one or more of Examples 1-7 optionally include receiving the signal at the interrogation device through a relay antenna.

Each of these non-limiting examples can stand on its own, or can be combined in various permutations or combinations with one or more of the other examples.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A surgical sensor system for collecting internal patient data, the surgical sensor system comprising:
   a sensor module comprising:
      a housing; and
      a sensor disposed within the housing; and
   a first attachment device comprising:
      a first socket for receiving the housing such that a portion of the housing remains exposed outside of the first attachment device in order to be exposed to anatomy when implanted; and
      an exterior anchor feature for attaching the first attachment device to biological matter.

2. The surgical sensor system of claim 1, wherein the first attachment device comprises a tapered body configured to engage an intramedullary canal of a long bone.

3. The surgical sensor system of claim 2, further comprising a first prosthetic implant having a second socket to receive the portion of the housing extending from the first socket.

4. The surgical sensor system of claim 3, wherein the first prosthetic implant comprises a tibial tray or a femoral component.

5. The surgical sensor system of claim 4, further comprising a second prosthetic implant having a third socket to receive the portion of the housing extending from the first socket, the second prosthetic implant having a different exterior form factor than the first prosthetic implant.

6. The surgical sensor system of claim 5, further comprising a second attachment device having a different exterior form factor than the first attachment device, the second attachment device having a fourth socket shaped similarly as the first socket of the first attachment device.

7. The surgical sensor system of claim 3, wherein the first prosthetic implant is uncoupled from the second socket such that the sensor module and first attachment device are spaced apart from the first prosthetic implant when implanted.

8. The surgical sensor system of claim 1, wherein:
the housing comprises an elongate body having a rounded end and a fastener portion opposite the rounded end, and one or more threads extending between the rounded end and the fastener portion;
the fastener portion comprises a hex head for receiving an insertion tool; and
the first socket comprises a rounded seat configured to mate with the rounded end.

9. The surgical sensor system of claim 1, wherein the sensor module further comprises: a lead connected to the sensor and extending out of an exterior of the housing, wherein the first socket comprises an opening to allow the lead to pass through the first attachment device.

10. The surgical sensor system of claim 7, further comprising a lead wire extending from the housing to extend along the first prosthetic implant, wherein the lead wire extends a sensing capability of the sensor module outside of the housing.

11. The surgical sensor system of claim 9, wherein the lead comprises a recharging cable for a rechargeable battery disposed within the housing.

12. The surgical sensor system of claim 9, wherein the housing comprises an opening to allow fluid into the housing to interact with the sensor or to allow electrodes of the sensor to interact with biological matter.

13. The surgical sensor system of claim 1, wherein the sensor module further comprises a plurality of fixation features on an exterior of the housing.

14. The surgical sensor system of claim 13, wherein the plurality of fixation features comprises elongate ribs.

15. The surgical sensor system of claim 1, wherein the exterior anchor feature comprises at least one of:
threading extending around the first attachment device; and
projections extending from an exterior wall of the first attachment device.

16. The surgical sensor system of claim 1, wherein the housing of the sensor module protrudes from the first socket when assembled with the first attachment device.

17. The surgical sensor system of claim 1, wherein the housing is divided into a plurality of modular components each modular component comprising a housing that is sealed to prevent fluid ingress and having ports for communicating electrical signals.

18. The surgical sensor system of claim 17, wherein the plurality of modular components comprises:
a communications module; and
a first sensing module having a first sensing capability.

19. The surgical sensor system of claim 18, further comprising a second sensing module having a second sensing capability different than the first sensing capability.

20. The surgical sensor system of claim 18, wherein the communications module comprises an elongate flexible lead extending from the housing.

* * * * *